US008118802B2

(12) United States Patent
Brandenburger et al.

(10) Patent No.: US 8,118,802 B2
(45) Date of Patent: Feb. 21, 2012

(54) CONNECTOR FOR PACKAGING CONTAINING MEDICAL FLUIDS AND PACKAGING FOR MEDICAL FLUIDS

(75) Inventors: Torsten Brandenburger, Niddatal (DE); Ismael Rahimy, Friedberg (DE)

(73) Assignee: Fresenius Kabi Deutschland GmbH, Bad Homburg (DE)

( * ) Notice: Subject to any disclaimer, the term of this patent is extended or adjusted under 35 U.S.C. 154(b) by 83 days.

(21) Appl. No.: 12/858,627

(22) Filed: Aug. 18, 2010

(65) Prior Publication Data

US 2011/0022024 A1 Jan. 27, 2011

Related U.S. Application Data

(63) Continuation of application No. 10/514,817, filed as application No. PCT/EP03/01847 on Feb. 24, 2003, now Pat. No. 7,828,787.

(30) Foreign Application Priority Data

May 27, 2002 (DE) .................................. 102 23 560

(51) Int. Cl.
*A61M 5/32* (2006.01)

(52) U.S. Cl. ........ 604/411; 604/408; 604/409; 604/410; 383/107; 383/109; 206/219; 206/484

(58) Field of Classification Search ........... 604/408–411
See application file for complete search history.

(56) References Cited

U.S. PATENT DOCUMENTS

| | | | | |
|---|---|---|---|---|
| 3,136,440 | A | 6/1964 | Krug et al. | 215/47 |
| 3,900,028 | A | 8/1975 | McPhee | 128/272 |
| 4,516,977 | A | 5/1985 | Herbert | 604/415 |
| 5,088,995 | A | 2/1992 | Packard et al. | 604/415 |
| 5,259,843 | A | 11/1993 | Watanabe et al. | 604/256 |
| 5,896,989 | A | 4/1999 | Ropiak et al. | 206/438 |
| 6,039,718 | A | 3/2000 | Niedospial, Jr. | 604/408 |
| 6,893,428 | B2 | 5/2005 | Willemstyn | 604/533 |

FOREIGN PATENT DOCUMENTS

| | | | |
|---|---|---|---|
| CA | 2179410 | | 7/1995 |
| DE | 14 98 600 | | 3/1941 |
| DE | 35 43 825 | A1 | 6/1986 |
| DE | 3543825 | | 6/1986 |
| DE | 197 28 775 | A1 | 1/1999 |
| DE | 694 16 696 | T2 | 9/1999 |
| DE | 69416696 | | 9/1999 |
| DE | 100 30 474 | C1 | 2/2002 |
| EP | 737 058 | B1 | 10/1996 |
| WO | 94/03373 | | 2/1994 |
| WO | WO 95/17873 | | 7/1995 |
| WO | WO 96/23545 | | 8/1996 |

*Primary Examiner* — Tatyana Zalukaeva
*Assistant Examiner* — Ilya Treyger
(74) *Attorney, Agent, or Firm* — Occhiuti Rohlicek & Tsao LLP

(57) ABSTRACT

The disclosure relates to a connector for packaging containing medical fluids, in particular infusion or transfusion bags, including a tubular connection part for receiving a spike for the withdrawal of fluid, and having a lower opening on the packaging side and an upper opening on the connection side. A self-sealing membrane, which is pierced by the spike, is located in the connection part. The membrane has an upper, annular section leading into a lower, plate-shaped section, said annular section of the membrane surrounding the spike in a sealing manner, when the latter pierces the plate-shaped section. The membrane acts as a guide for the spike and also reseals the connector, once the spike has been removed.

17 Claims, 3 Drawing Sheets

CONNECTOR FOR PACKAGING CONTAINING MEDICAL FLUIDS AND PACKAGING FOR MEDICAL FLUIDS

CROSS-REFERENCE TO RELATED APPLICATIONS

This application is a continuation of U.S. application Ser. No. 10/514,817, filed on Nov. 12, 2004, which is a U.S. national phase of International Application No. PCT/EP03/01847 filed Feb. 24, 2003, which claims priority to German Application No. 102 23 560.0, filed May 27, 2002. The entire disclosure of each of the above-identified applications is incorporated herein by reference.

BACKGROUND

The disclosure relates to a connector for packaging containing medical fluids, in particular infusion or transfusion bags, which serves to extract a fluid from the bag. Moreover, the disclosure relates to packaging for medical fluids, in particular an infusion or transfusion bag, with such a connector.

RELATED TECHNOLOGY

WO 96/23545 describes an infusion bag with an injection part and an extraction part. The injection part serves to feed a drug by means of an injection syringe. It comprises a tubular connection part, which is sealed by a protective cap designed as a break-off part. A self-sealing septum sits in the opening area of the connection part, whilst a membrane capable of being pierced is arranged in the connection part, so that the septum does not come into contact with the solution before the use of the infusion bag. The extraction part serves to extract the solution by means of a spike. The extraction part does not have a self-sealing septum, otherwise the structure is similar to that of the injection part.

A connector for the extraction of an infusion solution is also described in DE 197 28 775 C2. The tubular connection part of the known extraction part is sealed by a flat membrane, which is in one piece with the connection part.

The known extraction parts have been tried and tested in practice. A drawback, however, consists in the fact that the infusion bag is not sealed again after the spike has been withdrawn. There is therefore the risk of the infusion solution running out. This is particularly critical after the addition of cytostatic drugs.

A further drawback is that the connection between the spike and the extraction part is not secured against slipping out. When the bag is hanging on the stand, there is the risk of the connection of the spike arid the extraction part being separated due to unintentional tugging on the flexible-tube line.

There is also the drawback that the injected membrane, which seals the connection part of the extraction part, does not always withstand greater mechanical loads. Thus, it has been shown in drop tests that the membrane of individual extraction parts ruptured.

SUMMARY

The problem underlying the disclosure is to provide a connector for packages containing medical fluid, in particular infusion or transfusion bags, which reliably seals the packaging after the withdrawal of the spike.

Accordingly, the disclosure provides a connector for packages containing medical fluids, including a tubular connection part for receiving a spike for the extraction of the fluid, the connection part having upper and lower openings, a break-off sealing part, a self-sealing membrane that can be pierced by the spike for the extraction of the fluid and having a circular upper portion, which transforms into a dish-shaped lower portion to form a trough-shaped recess, wherein a portion of the membrane sealing surrounds the spike when the spike pierces the dish-shaped portion.

DETAILED DESCRIPTION

Figure 1:
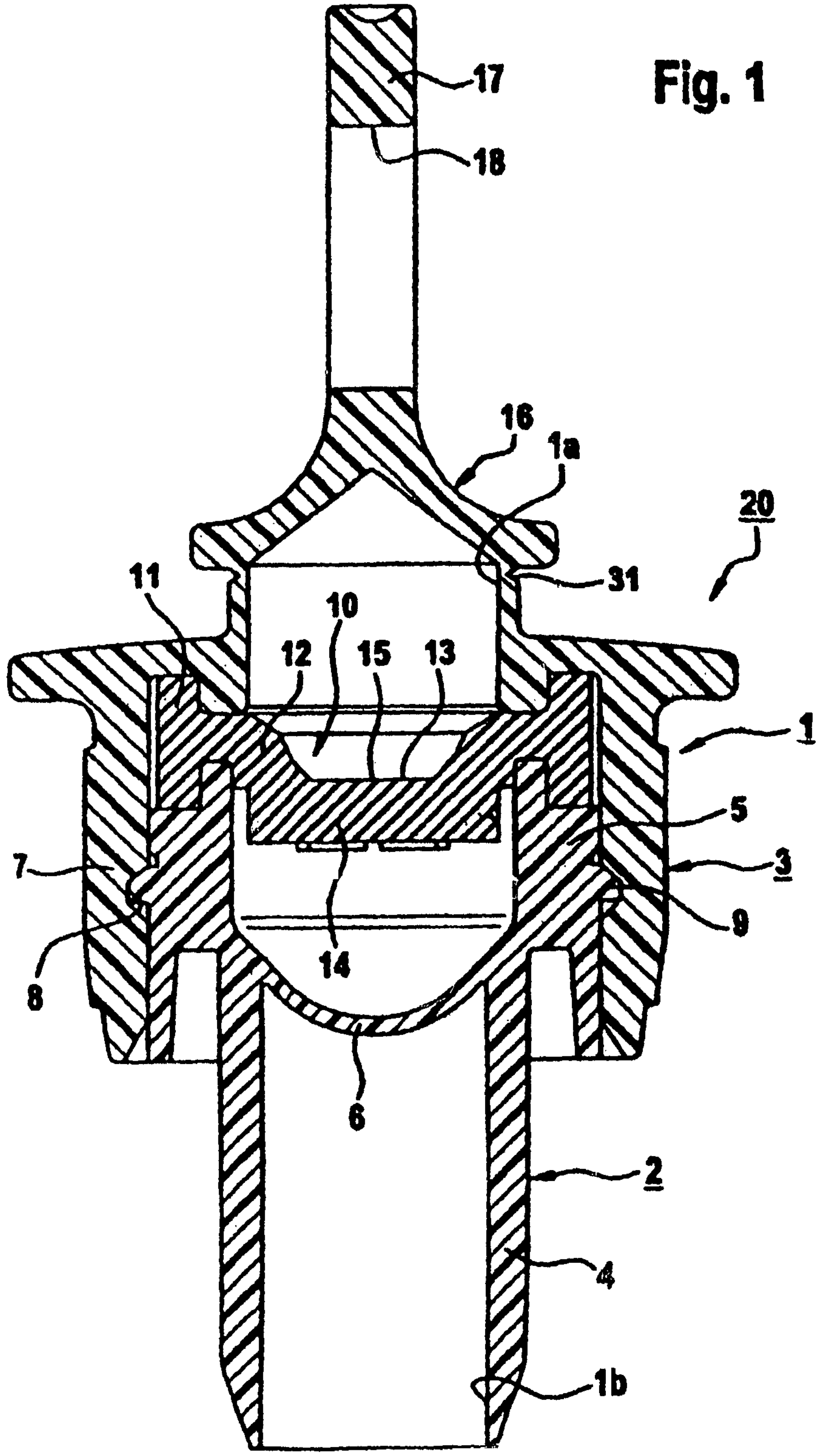
FIG. 1 illustrates a connector designed as an extraction part for packages containing medical fluids in sectional representation.

The connector according to the disclosure has a self-sealing membrane, which is arranged in the connection part for accommodating the spike for the extraction of the fluid. The self-sealing membrane prevents the fluid from running out of the packaging after withdrawal of the spike.

It is advantageous that the self-sealing membrane has a circular portion, which transforms into a dish-shaped portion, whereby the circular portion of the membrane surrounds the spike in a sealed manner when it pierces the dish-shaped portion.

The special formation of the membrane with the circular and dish-shaped portion on the one hand ensures that the spike is guided reliably when it pricks the membrane and on the other hand guarantees that the membrane is again reliably sealed after withdrawal of the spike even in the presence of relatively high internal pressure in the packaging. It has been shown in tests that the special formation of the membrane is decisive for immediate re-sealing, whereby the sealing of the membrane is further enhanced with increasing pressure in the packaging. The reliable sealing can be traced back not to the volume of material, but to the special geometry of the membrane.

In a preferred form of embodiment of the connector, the material of the dish-shaped portion of the membrane is weakened, so that the membrane can be particularly easily pierced by the spike. The membrane is preferably pre-slit in the form of a cross. It can also be pre-slit in the form of a star or only be provided with a simple slit.

In a particularly preferred form of embodiment, the tubular connection part of the connector consists of a lower and an upper section, whereby the sections are fixed in a snap-in manner. The self-sealing membrane is preferably held clamped with elastic deformation of the same between the lower and upper section. Consequently, the fitting of the connector can be carried out in a straightforward manner by pressing of the individual parts. It is however also possible for the individual parts to be welded and/or glued together.

A further particularly preferred form of embodiment makes provision such that an outer portion, which is clamped between the two sections, follows on from the circular portion of the membrane.

In order to prevent the self-sealing membrane in the tubular connection piece from coming into contact with the solution contained in the infusion and transfusion bag prior to the use of the latter, a second membrane capable of being pierced is preferably arranged beneath the self-sealing membrane thereby forming an intermediate space. The second membrane is expediently a one-piece component of the tubular connection piece.

It has been shown in tests that the use of a membrane curved upwards or downwards instead of a flat membrane leads to an increase in drop strength. Since the second membrane is designed curved upwards or downwards, the connector according to the invention withstands relatively great mechanical loads. Apart from the increase in drop strength, there is also the advantage that the spike in the pierced position is held clamped by the curved membrane. The retention force of the spike in the withdrawal position is thus increased, as a result of which unintentional slipping out is prevented.

In order to secure the upper and lower part of the connection piece against radial torsion, both parts can have toothing or the like, which also ensures precise alignment of the parts during pressing together. Furthermore, the risk of damage to the two membranes is especially low during the pressing together of the individual parts.

The break-off sealing part of the connector, which serves as an originality seal, is preferably connected to the connection part via a circular rupture zone.

Since the break-off sealing part preferably has a grip part, which is designed in the manner of an arrow pointing upwards, it can immediately be recognized that the connector is an extraction part, but not an injection part. Preferably, the arrow is a recess in the grip part, which is immediately recognizable without lettering or the like being necessary. Confusion between the extraction and injection part of a package containing medical fluids can thus be avoided.

The lower part of the connection piece also preferably has an arrow pointing upwards, which is designed as a raised structure, preferably in a recessed grip. The upward-pointing arrow of the lower connection-piece part also permits the connector to be unequivocally assigned as the extraction part after breaking-off of the sealing part.

An example of an embodiment is explained in greater detail below by reference to the drawings.

Connector 20 designed as an extraction part for packages containing medical fluids, in particular infusion or transfusion bags, has a tubular connection part 1, which includes a package-side lower section 2 and a connection-side upper section 3. Tubular connection part 1 therefore has an upper and a lower opening 1*a*, 1*b*. Connector 20 is an injection-moulded part made of polypropylene.

Lower section 2 of tubular connection part 1 has a lower cylindrical portion 4, which transforms into an upper sleeve-shaped portion 5. Cylindrical portion 4 of lower section 2 can be inserted into a connection socket of a film bag and can be welded or glued to the socket or be directly welded into the film bag without a socket. Cylindrical portion 4 is sealed at its upper end with a membrane 6 capable of being pierced, said membrane being a single-piece component of lower section 2. The injected membrane is curved downwards. Alternatively, however, the membrane can also be curved upwards.

Upper section 3 of tubular connection part 1 is fixed in a snap-in manner on lower section 2, whereby upper section 3 has a cylindrical portion 7 which surrounds lower section 2. The internal wall of cylindrical portion 7 of upper section 3 has a peripheral groove 8, into which a peripheral projection 9 on the outer wall of sleeve-shaped portion 5 of lower section 2 snaps when the two sections 2, 3 are pressed together.

A self-sealing membrane 10 made of an elastic material, which is also referred to as a septum, is held clamped with elastic deformation of the same between the lower and upper section 2, 3 of tubular connection part 1. Self-sealing membrane 10 has an outer portion 11, which is clamped between lower and upper sections 2, 3 of circular connection part 1. Outer portion 11 is followed by an upper circular portion 12, which transforms into a lower dish-shaped portion 14 thereby forming a trough-shaped recess 13 at the upper side of membrane 10. Dish-shaped portion 14 is pre-slit in the form of a cross or a star in centre 15, so that the elastic material is weakened, but is not severed.

Upper section 3 of tubular connection part 1 is followed, via a circular rupture zone 31, by a cap-shaped sealing part 16, which seals upper opening 1*a* of connection part 1. Sealing part 16 transforms into a flat grip part 17, which is provided with a recess 18 in the shape of an arrow 19 pointing upwards. It can immediately be recognized from the direction of arrow 19 that connector 20 is not injection part 40, but rather the extraction part.

Figure 2:
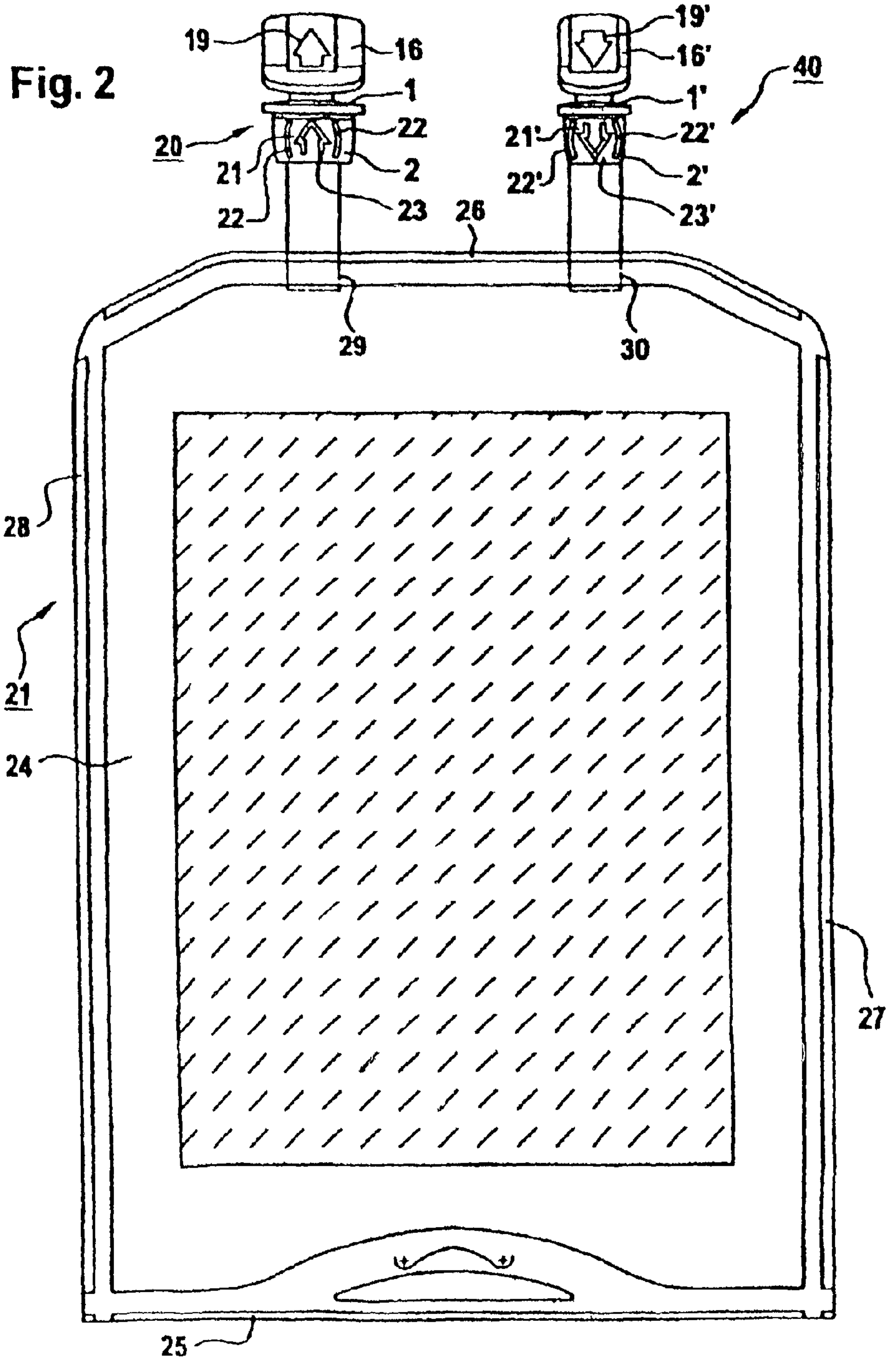
FIG. 2 illustrates an infusion bag with the extraction part of FIG. 1 and an injection part and FIG. 3 illustrates the injection part of the infusion bag of FIG. 2 in sectional representation.

The side view of connector 20 of FIG. 1 is shown in FIG. 2. FIG. 2 shows an infusion bag 21 filled with infusion solution, which has connector 24 for the extraction of the infusion solution and a further connector 40 for the injection of a solution into infusion bag 21.

On the outer wall of cylindrical portion 7 of upper section 3, tubular connection part 1 of connector 20 has two recessed grips 21 lying opposite one another, which are each formed by projecting webs 22 which are arranged at a distance from one another. A further arrow 23, which also points upwards in order to identify connector 20 as the extraction part, is formed as a raised structure on the outer wall of cylindrical portion 7 between webs 22.

Infusion bag 21 comprises two film layers 24, which are welded together at lower and upper edge 25, 26 and also at longitudinal edges 27, 28. Two connections sockets 29, 30 are welded into upper edge 25 of the infusion bag. The tubular connection pieces of injection and extraction part 40, 20 are inserted into connection sockets 29, 30 and connected with the sockets during sterilization. The tubular connection pieces of the originality seals can however also be molded onto an insert that is round or designed in the manner of a boat, said insert being welded in between the two film layers.

Figure 3:
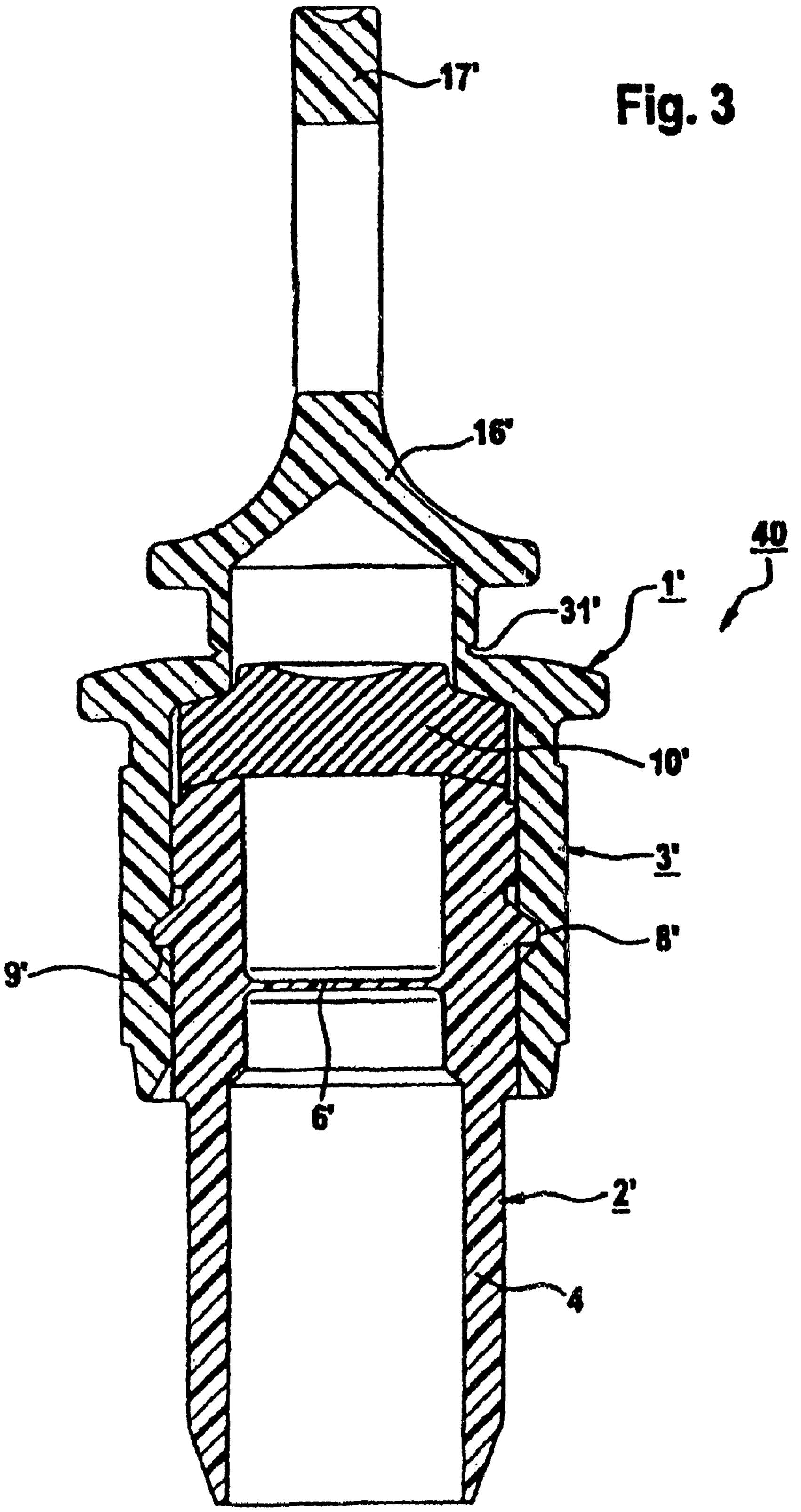

FIG. 3 shows injection part 40 of film bag 21 in a sectional representation. Injection part 40 has a similar structure to extraction part 20. The parts corresponding to one another are therefore provided with the same reference numbers. Injection part 40 has a tubular connection part 1', which consists of a lower and an upper section 2', 3'. The two sections 2', 3' are fixed in a snap-in manner with the interposition of a self-sealing membrane 10', whereby a projecting shoulder 8' of lower section 2' engages in a groove 9' of upper section 3'. Flat membrane 6', which however can also be curved, is injected into lower section 2'.

Upper section 3' of tubular connection part 1' is again followed, via a circular rupture zone 31', by a cap-shaped break-off part 16', which transforms into a flat grip part 17'. An arrow 19' pointing downwards is designed as a recess in grip part 17'. Arrows 23' pointing downwards to indicate the flow direction are located on the outer wall of upper section 3' again inside recessed grips 21'.

For the extraction of infusion solution, break-off part 16 of extraction part 20 is broken off by turning or breaking the same, so that self-sealing membrane 2 is laid bare. The spike of a known transfer system is pushed into tubular connection part 1 of extraction part 20, as a result of which pre-slit membrane 10 is pierced and membrane 6 curved downwards is penetrated. Trough-shaped recess 13 serves as a guide for the spike. The spike is sealed by circular portion 12 of membrane 10. On account of the special formation of injected membrane 6, the spike is held firmly in tubular connection part 1.

The infusion solution can then be extracted. When the spike is again withdrawn, self-sealing membrane 10 reliably seals extraction part 20 even in the presence of a relatively high internal pressure. Moreover, the mechanical strength of extraction part 20 is increased by the special formation of injected membrane 6.

Injection part 40 serves to inject an active substance into the infusion solution. For this purpose, self-sealing membrane 10' and injected membrane 6' are again pierced with the injection needle of a syringe after removal of break-off part 16'. The injection part is again sealed after withdrawal of the needle.

It is to be understood that the foregoing description is intended to illustrate and not to limit the scope of the invention, which is defined by the scope of the appended claims. Other embodiments are within the scope of the following claims.

What is claimed is:

1. A self-sealing membrane disposed within a connector of a medical fluid container, the self-sealing membrane comprising:

a penetrable section; and a flange configured to be clamped between a lower section of the connector and an upper section of the connector, the flange having a generally T-shaped cross-sectional profile formed by an inner segment that extends from a boundary of the penetrable section, and an outer segment that extends from a boundary of the inner segment.

2. The self-sealing membrane of claim 1, wherein the flange is configured to be clamped with elastic deformation between the lower section of the connector and the upper section of the connector.

3. The self-sealing membrane of claim 1, wherein the penetrable section and the flange together have a generally H-shaped cross-sectional profile when the penetrable section is disposed across a fluid passageway defined by the connector.

4. The self-sealing membrane of claim 1, wherein the penetrable section is generally dish-shaped.

5. The self-sealing membrane of claim 1, wherein:

the inner segment of the flange is defined by an upper surface area and a lower surface area separated no more than a first distance $d_{inner}$; and the outer segment of the flange is defined by an upper surface area and a lower outer surface area separated no more than a second distance $d_{outer}$, wherein the second distance $d_{outer}$ is greater than the first distance $d_{inner}$.

6. The self-sealing membrane of claim 5, wherein the upper surface area of the inner segment and the lower surface area of the inner segment are separated by the first distance $d_{inner}$.

7. The self-sealing membrane of claim 5, wherein the upper surface area of the outer segment and the lower surface area of the outer segment are separated by the first distance $d_{outer}$.

8. The self-sealing membrane of claim 1, wherein:

the inner segment of the flange is defined by a first annular volume; and the outer segment of the flange is defined by a second annular volume.

9. A connector for a medical fluid container, the connector comprising:

a first section having a peripheral groove on a portion of an internal wall; and a second section having a peripheral projection on a portion of an external wall, wherein each of the first section of the connector and the second section of the connector is sized and dimensioned to:

achieve a snap-in effect when the peripheral projection of the second section is disposed within the peripheral groove of the first section, and accommodate a self-sealing membrane having a generally H-shaped cross-sectional profile.

10. The connector of claim 9, wherein the self-sealing membrane includes a flange that has a generally T-shaped cross-sectional profile.

11. The connector of claim 9, wherein the self-sealing membrane includes a flange that is formed by:

an inner segment that is defined by an upper surface area and a lower surface area separated no more than a first distance $d_{inner}$; and an outer segment that is defined by an upper surface area and a lower outer surface area separated no more than a second distance $d_{outer}$, wherein the second distance $d_{outer}$ is greater than the first distance $d_{inner}$.

12. The connector of claim 9, wherein the self-sealing membrane includes a flange that is formed by and inner annular volume and an outer annular volume.

13. The connector of claim 9, wherein the self-sealing membrane includes a penetrable section that is disposed at an intersection of the first section of the connector and the second section of the connector.

14. The connector of claim 13, wherein the penetrable section is generally dish-shaped.

15. The connector of claim 9, wherein the self-sealing membrane includes a penetrable section that is disposed across a fluid passageway defined by the connector.

16. The connector of claim 15, wherein the penetrable section is generally dish-shaped.

17. The connector of claim 9, wherein the self-sealing membrane is held clamped with elastic deformation between the first section of the connector and the second section of the connector.

* * * * *